United States Patent [19]

Boshier

[11] Patent Number: 5,311,639
[45] Date of Patent: May 17, 1994

[54] SYSTEM FOR DETECTING AND REMOVING FOREIGN OBJECT DEBRIS

[75] Inventor: Geoffrey C. Boshier, Greenbrier, Tenn.

[73] Assignee: Avco Corporation, Providence, R.I.

[21] Appl. No.: 67,722

[22] Filed: May 26, 1993

[51] Int. Cl.$^5$ .............................................. A47L 9/02
[52] U.S. Cl. ......................................... 15/324; 15/339; 15/414; 15/415.1; 356/241
[58] Field of Search .............. 15/339, 414, 324, 415.1, 15/304; 356/241

[56] References Cited

U.S. PATENT DOCUMENTS

| | | | |
|---|---|---|---|
| 2,740,153 | 4/1956 | Bishop | 15/415.1 |
| 3,841,764 | 10/1974 | Snell et al. | 356/241 |
| 3,896,793 | 7/1975 | Mitsui et al. | 128/6 |
| 3,924,608 | 12/1975 | Mitsui | 128/2 B |
| 3,938,218 | 2/1976 | DeAmicis | 15/414 X |
| 4,253,697 | 3/1981 | Acosta | 294/115 |
| 4,277,168 | 7/1981 | Oku | 356/241 X |
| 4,530,568 | 7/1985 | Haduch et al. | 350/96.26 |
| 4,735,501 | 4/1988 | Ginsburgh et al. | 356/241 |
| 4,747,405 | 5/1988 | Leckrone | 128/303.1 |
| 4,792,276 | 12/1988 | Krawiec et al. | 415/118 |
| 5,072,487 | 12/1991 | Walton | 15/304 X |
| 5,195,209 | 3/1993 | Watkins | 15/339 |
| 5,205,174 | 4/1993 | Silverman et al. | 15/339 X |

FOREIGN PATENT DOCUMENTS 865757 4/1961 United Kingdom ........... 15/414

Primary Examiner—Chris K. Moore
Attorney, Agent, or Firm—Perman & Green

[57] ABSTRACT

A system for detecting and removing foreign object debris from an enclosed region is capable of insertion through a small-sized opening. A source of light is optically transmitted through a first window in the outer peripheral surface of an elongated borescope adjacent its distal end to illuminate a debris containing region. An image of the region is transmitted through a second window in the distal end of the borescope to a remote television monitor. A vacuum conduit extends to a flexible tip end which is proximate to the distal end of the borescope and is connected to a source of vacuum to create a suction at the tip end. An elongated guide sleeve serves to slidably receive the vacuum conduit. The tip end of the vacuum conduit is movable relative to the guide sleeve between a retracted position substantially coincident with the first end of the guide sleeve and an extended position whereat the tip end of the vacuum conduit is distant from the first end. The first end of the guide sleeve can be articulated from a neutral position aligned with its longitudinal axis and an operating transverse position such that the flexible tip end of the vacuum conduit is similarly turned. Additionally, the guide sleeve is rotatable about its longitudinal axis to thereby position the tip end of the vacuum conduit proximate to the debris when the tip end is in the operating position for withdrawal of the debris for disposal.

10 Claims, 2 Drawing Sheets

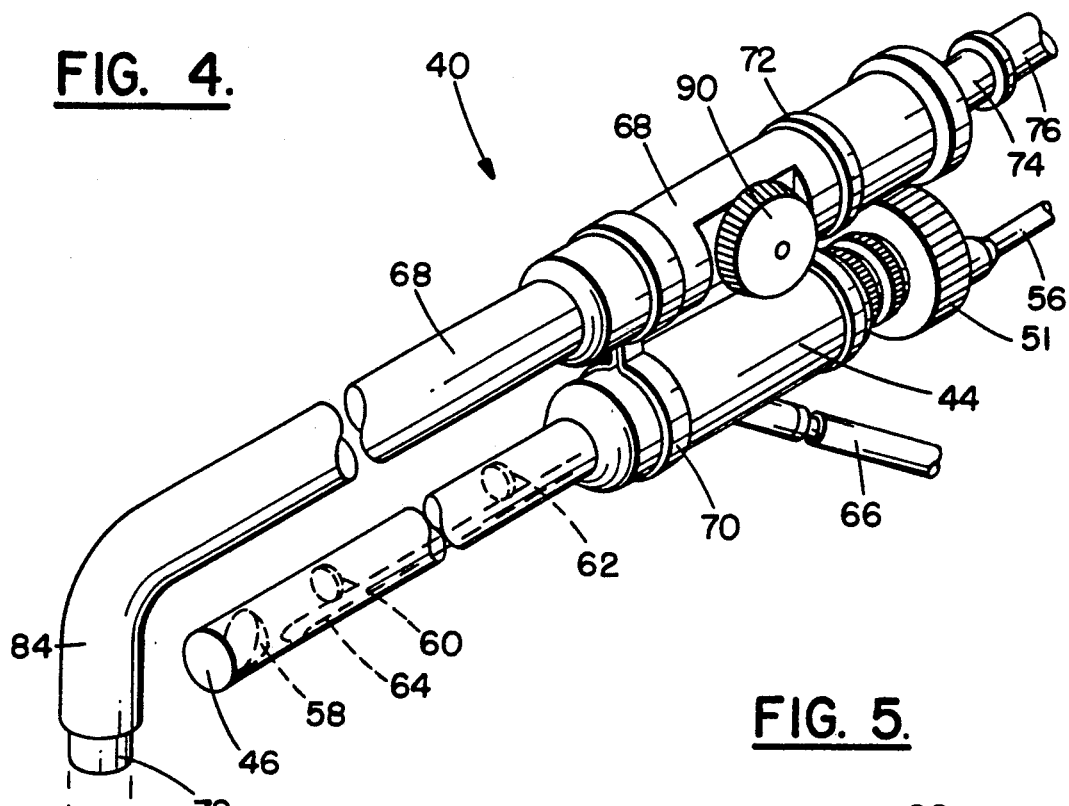
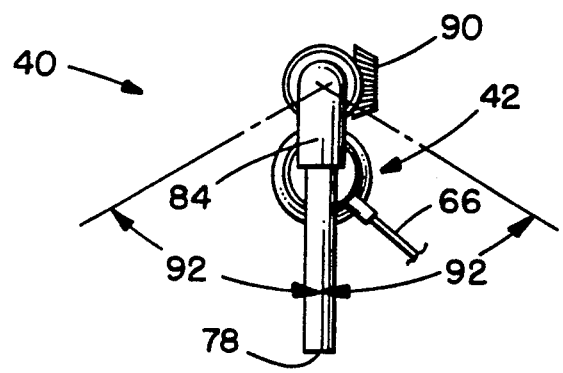
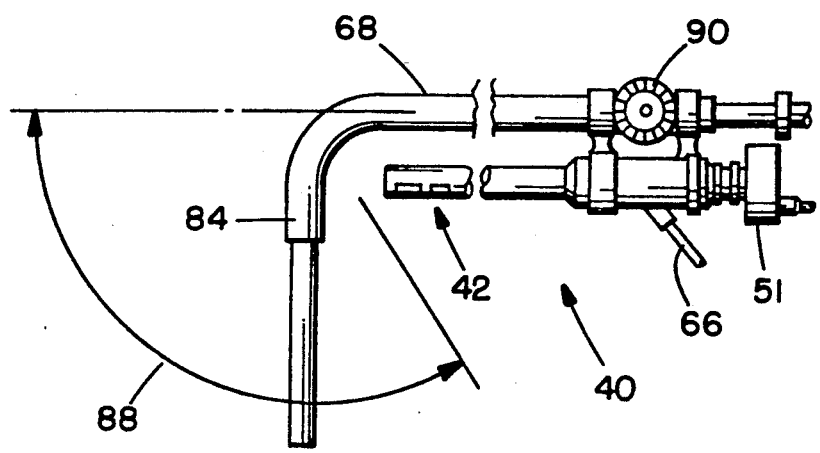

SYSTEM FOR DETECTING AND REMOVING FOREIGN OBJECT DEBRIS

BACKGROUND OF THE INVENTION a. Field of the Invention

The present invention relates to an integrated system for detecting and removing undesired debris from the interior of an enclosed structure such as an aircraft wing after it has been manufactured but before it is placed in service.

b. Description of the Prior Art

In recent years, elongated optical devices have been developed which are capable of transmitting visual images to a remote observer. These devices are used to transmit images of objects near the distant end of the device to an observer at the near end of the device. This permits the observer to perform a visual inspection of remote objects within the field of view of the far end of the device. The original devices were used to inspect the bores of guns, hence the name borescopes. Other common names applied to such devices are endoscopes and intrascopes. Presently borescopes are used to facilitate inspection of a large variety of objects located in remote, inaccessible or hazardous areas. Thus, they are used in such diverse applications as the inspection of turbine engines, human bodies, and nuclear reactors.

The first borescopes were essentially elongated tubular microscopes which employed a series of lenses to convey an image of an object in the field of view of a field lens at a remote end of the tube to an objective lens at the observer's end of the tube. Usually, means were also provided to illuminate the field of view of the borescope, as for example by a small lamp located near the remote end of the tube.

Modern borescopes oftentimes utilize flexible fiber optic cables rather than lenses. The fiber optic cables contain parallel bundles of fine transparent fibers, and transmit to one end of the cable an image of the area within the field of view of the opposite end of the cable.

Most fiber optic borescopes have a flexible protective sheath covering the entire length of the cable. Typically, the sheath is made of a durable, abrasive resistant material such as a woven metal. Also, most fiber optic borescopes include within the sheath a second fiber optic cable which is illuminated by a bright light source at the observer's end. The second cable transmits light to the remote end of the cable, which then illuminates the field of view of the imaging fiber optic cable.

A relatively recent improvement in fiber optic borescopes permits the observer at the viewing end of the borescope to remotely manipulate the distant end of the cable to position the axis of the imaging fiber optic cable at a desired orientation, thereby bringing into its field of view a desired area of interest. These remotely manipulatable fiber optic borescopes are referred to as articulated, articulating or articulateable borescopes. By applying tension to one or more flexible wires strung through the protective sheath and attached to a pivotable member near the remote end or head of the cable, the head may be tilted at an angle to the longitudinal axis of the cable. Such borescopes can have either one or two planes of articulation. The latter type permits aiming the head of the borescope to any point in a forward directed hemisphere (or larger portion of a sphere) centered around the head end of the cable.

Typical of the prior art disclosing such elongated inspection systems are U.S. Pat. No. 4,735,501 to Ginsburgh et al. and No. 4,530,568 to Haduch et al. which are particularly adept at gaining entry to inaccessible regions. U.S. Pat. No. 4,277,168 to Oku discloses such a device which includes a television monitor for viewing, from a remote location, the progress being made by the endoscope. In U.S. Pat. No. 3,924,608 to Mitsui, an endoscope is disclosed for insertion into a body cavity. The endoscope is provided with forceps to excise body tissue for subsequent inspection and with a suction conduit for removal of the body tissue for the inspection procedure. U.S. Pat. No. 4,747,405 to Leckrone discloses an angioplasty catheter provided with a laser for vaporizing undesired material and a blade for excising undesired material and a suction duct for removal of the vaporized or excised material. U.S. Pat. No. 4,792,276 to Krawiec et al. discloses apparatus for locating and removing debris or foreign material located in the bladed region of a turbomachine.

It was with recognition of the prior art as described above that the present invention was conceived and has now been reduced to practice.

SUMMARY OF THE INVENTION

According to the invention, a system is provided for detecting and removing foreign object debris from an enclosed region. The system includes an elongated borescope which is capable of insertion through a small-sized opening into the enclosed region. A source of light is optically transmitted through a first window in the outer peripheral surface of the borescope adjacent its distal end to illuminate a debris containing region. An image of the region is transmitted through a second window in the distal end of the borescope to a remote television monitor. A vacuum conduit extends to a flexible tip end which is proximate to the distal end of the borescope and is connected to a source of vacuum to create a suction at the tip end. An elongated guide sleeve serves to slidably receive the vacuum conduit. The tip end of the vacuum conduit is movable relative to the guide sleeve between a retracted position substantially coincident with the first end of the guide sleeve and an extended position whereat the tip end of the vacuum conduit is distant from the first end. The first end of the guide sleeve can be articulated from a neutral position aligned with its longitudinal axis and an operating transverse position such that the flexible tip end of the vacuum conduit is similarly turned. Additionally, the guide sleeve is rotatable about its longitudinal axis to thereby position the tip end of the vacuum conduit proximate to the debris when the tip end is in the operating position for withdrawal of the debris for disposal.

Thus, an integrated system has been devised which particularly addresses the detection and removal of foreign object debris (FOD) from enclosed aircraft structures. The equipment combines remote optical video viewing with a unique vacuum retrieval nozzle which can be guided manually to the point at which the debris resides in the structure. FOD can be classified as any piece of material that remains in a confined space which is not part of the specified design.

It is critical that all loose pieces of material are removed from within an aircraft structure, both during the manufacturing process and when the aircraft is in service. FOD inspection and removal operations or "sweeps" are incorporated throughout the build cycle of all major aircraft subassemblies. Items that are found in such sweeps include fasteners, clips, swarf, sealant and even mechanics' handtools and accessories. Undetected debris that is left to reside in aircraft wings, for example, can be particularly dangerous. Most modern aircraft use the "wingbox" as a fuel cell, two or more of which are interconnected one-to-another. Loose objects can cause malfunction of valves, filters, pumps and fuel lines. Catastrophic failure has resulted from inclusion of FOD within wing structures. The U.S. Department of Transportation and the U.S. aircraft industry in general treat the detection, isolation and removal of this damaging material as an extremely important operation.

Heretofore, aerospace practices for detecting and removing FOD included combinations of many creative yet primitive practices. Since packaged kits of FOD removal hardware have not been available, innovation became necessary, with individual operators creating their own system from readily available pieces of hardware. Such devices as mirrors attached to a length of wire and hand held flash lights combined with flexible vacuum lines were put together on an as needed basis. However, methods such as these require considerable operator dexterity and hand-eye coordination and, in most instances, such attempts were not successful.

A primary object of this invention, then, is to provide a readily available system which can remove FOD from a wide range of enclosed, difficult to reach, spaces. The system can operate through relatively small access ports or inspection holes. By packaging the equipment such that one operator can simultaneously control all the functions, having true (non-reverse) imaging with good definition and more positive collection of the debris, FOD detection and removal can become an efficient manufacturing operation. The system also provides for a final inspection sweep after all FOD has been removed; since a television image is available, inspectors can verify that a "clean" structure has been obtained.

In short, the invention provides the airframe mechanic with a complete system which can illuminate the enclosed structure, scan the area in which FOD resides, and then guide a retrieval nozzle to a close enough proximity that applied vacuum working through the nozzle can withdraw loose objects. Imaging is provided by a CCD type television camera mounted on the borescope. A small high resolution monitor can be positioned at a convenient location for the operator to control the manipulation of the borescope and retrieval nozzle.

Other and further features, advantages, and benefits of the invention will become apparent in the following description taken in conjunction wit following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts through the disclosure.

BRIEF DESCRIPTION OF THE DRAWINGS

FIG. 4 is a perspective view of the detection and removal system illustrated in FIG. 3;

FIG. 5 is a front elevation view of the system depicted in FIGS. 3 and 4 and indicating its arcuate range of movement in lateral directions; and FIG. 6 is a top plan view of the system illustrated in FIGS. 3, 4, and 5, and indicating its arcuate range of movement in a longitudinal direction.

DETAILED DESCRIPTION OF THE PREFERRED EMBODIMENT

Figure 1:
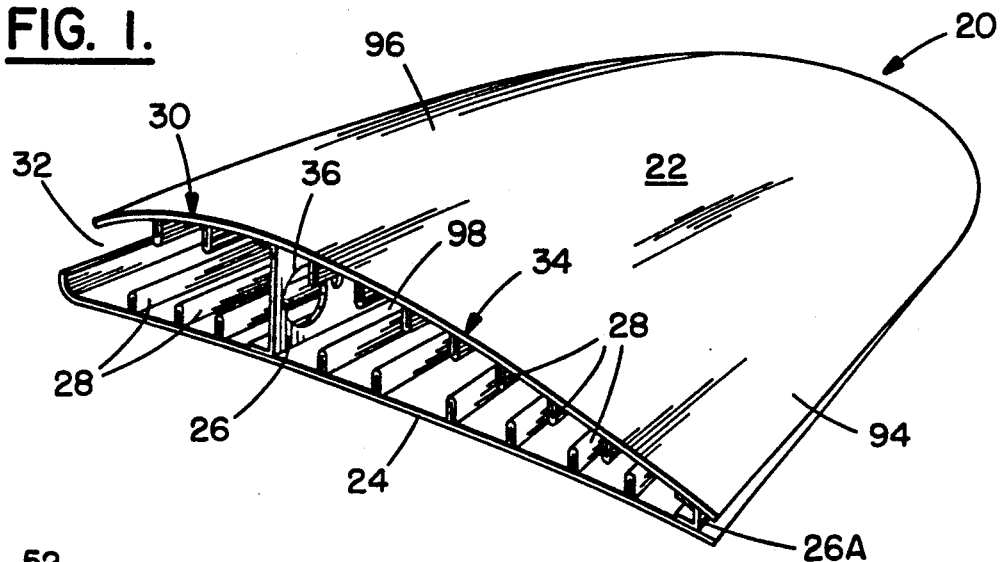
FIG. 1 is a perspective view, partially cut away and in section, diagrammatically illustrating a typical wing section of the type to be operated on by a system of the present invention.

Turn now to the drawings, and, initially, to FIG. 1 which depicts, diagrammatically, a cutaway of a typical wing section 20 which is nearing completion of the assembly process. For purposes of discussion, the wing section 20 comprises an upper skin 22, a lower skin 24, and a longitudinally extending front spar 26 and rear spar 26A extending substantially the length of the wing section and suitably jointed to the upper and lower skins 22, 24. The wing section 20 also includes a plurality of ribs (not shown) which extend transversely between the spars 26 and 26A at suitable intervals. In customary fashion, suitably joined to both the upper and lower skins 22, 24, are a plurality of longitudinally extending blades 28 extending at spaced locations and in directions which are substantially parallel with the spar 26. A primary function for the blades 28 is to provide tensile and compression stiffening for the wing section 20. The stiffened wing skins and attached ribs form enclosed box sections which act to provide torsional rigidity to the structure.

It will be appreciated that during the construction of the wing section 20, which is typical of other aircraft structures or subassemblies, loose pieces of material undesirably collect within the interior of the wing section. These may be, for example, fasteners, clips, swarf, sealant, and even hand tools. Such foreign object debris (FOD) can be dangerous if it remains undetected and permitted to remain within the aircraft structure. Such debris is free to move around within the confined space in which it resides when the aircraft is in flight undesirably causing noise, structural damage and, worse yet, potentially causing malfunctions of equipment within the aircraft structure including such critical items as valves, filters, pumps, and fuel lines. Indeed, catastrophic failure can result from the presence of such FOD.

Viewing FIG. 1, such FOD typically resides between adjacent blades 28, lying on an inner surface of the lower skin 24 when the wing section 20 is essentially in a horizontal position. In a leading edge region 30, there is little difficulty with retrieving FOD since there are usually a plurality of enlarged openings 32 available at the forward portion of the wing section 20 prior to mounting of finished leading edge covers (not shown). However, significant problems exist with respect to FOD located in a main wing box region 34, that is, in the region aft of the spar 26. Access to the main wing box region 34 can only be achieved through a plurality of spaced access holes 36 which are formed in the spar 26. These access holes 36 conventionally serve the purpose of weight reduction without effecting strength of the wing section 20.

Figure 2:
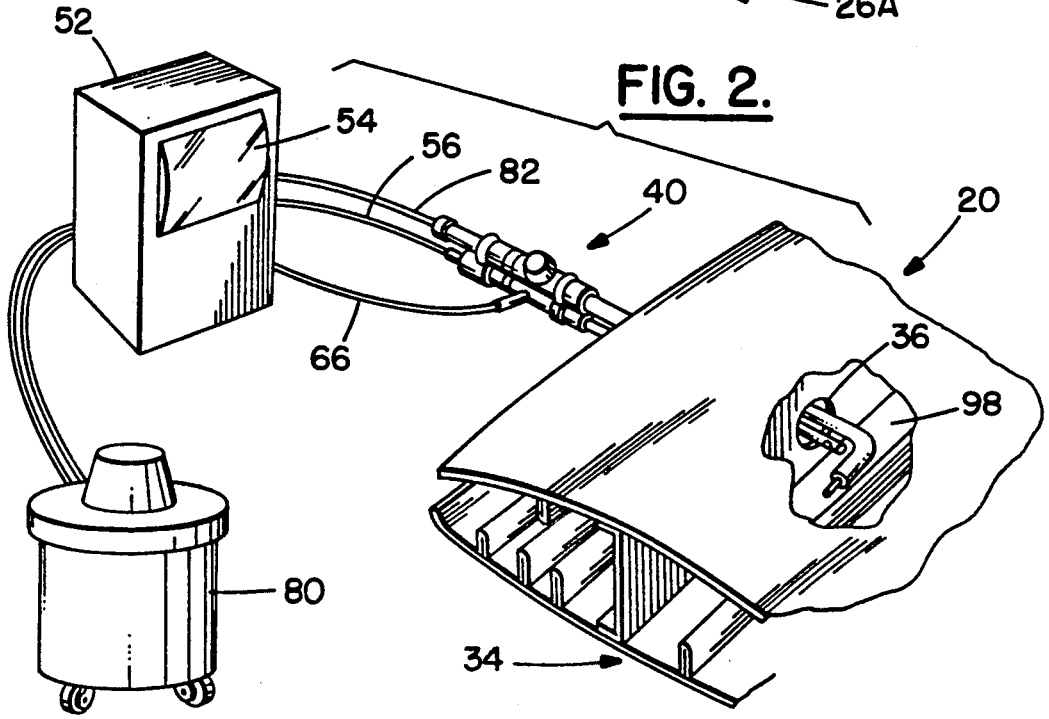
FIG. 2 is a perspective diagrammatic view illustrating the system of the invention operating on a wing section having the construction depicted in FIG. 1.

In FIG. 2, there is diagrammatically illustrated a detection and removal system 38 which includes components 40 which are capable of being inserted through the access holes 36 and of reaching into the rear box region 34 for detecting and removing foreign object debris from that enclosed region.

Turn now to FIGS. 3, 4, 5, and 6 for a more detailed description of the components 40. An elongated tubular borescope 42 extends between a proximal end 44 and a distal end 46 which is preferably rounded in order to more easily penetrate the access holes 36. A pair of windows 48, 50 are provided in the outer peripheral surface of the borescope 42 adjacent the distal end 46. The window 48 is optically aligned with an optical system including a television camera 51 which serves to transmit an image from regions external of the borescope 42 to a television monitor 52 remotely located from the main wing box region 34. An operator of the components 40 can thereby view on a screen 54 an image of a region to be inspected proximate to the distal end 46 of the borescope 42. In order to transmit the image through the window 48 to the screen 54, a suitable transmission line 56 is provided which, in turn, communicates with a suitable optical system schematically represented by a prism 58, aligned lenses 60, 62, and the camera 51. While a conventional lens system is depicted, it will be understood that it may be desirable to utilize a fiber optic system. In a similar fashion, the window 50 is optically in communication with a fiber optic bundle 64 which, in turn, communicates via transmission line 66 to a suitable light source (not shown). In this manner, the region to be inspected can be illuminated.

Figure 3:
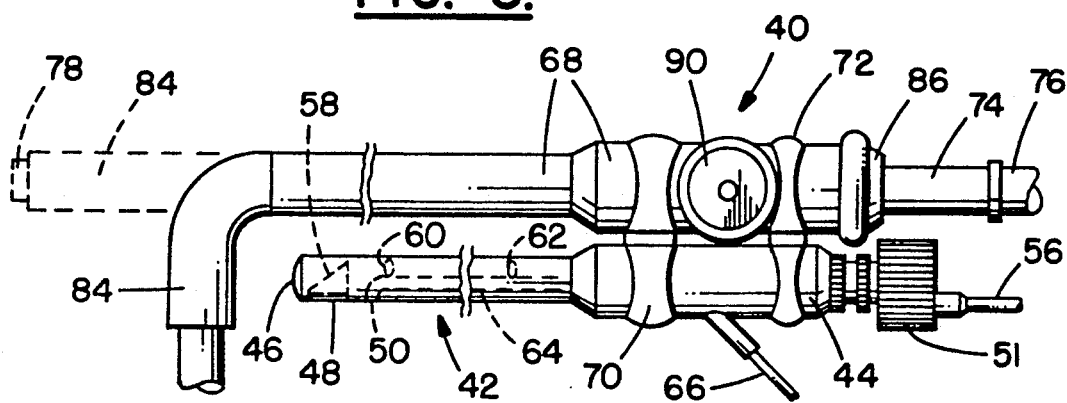
FIG. 3 is a top plan view depicting the detection and removal system of the invention.

With continued reference particularly to FIGS. 3 and 4, the components 40 are seen to include a guide sleeve 68 which is suitably mounted as by bearings 70, 72 in a side-by-side arrangement with the proximal end 44 of the borescope 42. A vacuum conduit 74 is slideably received within the guide sleeve 68 and extends between a near end 76 and a tip end 78 which is proximate to the distal end 46 of the borescope 42. The vacuum conduit 74 is operably connected to a source 80 of the vacuum via vacuum line 82 (FIG. 2). The source of vacuum 80 may be, for example, a "SHOP-VAC" brand vacuum cleaner, or equivalent.

While the guide sleeve 68 may be substantially rigid for most of its length, it has a first end portion 84 distant from its second end 86 which is capable of articulation between a first dashed line position (FIG. 3) which is aligned with a longitudinal axis of the major part of the guide sleeve 68 to a transverse, solid line position. In actual fact, as seen in FIG. 6, the tip end 78 may be articulatable through an arc 88 as depicted in FIG. 6.

As with the guide sleeve 68, a major length of the vacuum conduit 74 may be substantially rigid. However, the tip end 78 and, specifically, that portion of the vacuum conduit 74 which is generally coextensive with the first end portion 84 of the guide sleeve 68 is also articulatable. That is, as the first end portion 84 of the guide sleeve 84 is moved from a neutral position to a transverse position, the tip end 78 of the vacuum conduit 74 is caused to follow suit. A manually operable knob 90 mounted on the guide sleeve 68 provides the operator with a means for articulating the first end portion 84. This is achieved by means of a well known mechanism forming no part of the present invention.

As previously noted, the vacuum conduit 74 is slidably movable, longitudinally, relative to the guide sleeve 68, within limits. Thus, the tip end 78 can be withdrawn until it is substantially coextensive with the extreme end of the first end portion 84. Alternatively, the tip end 78 can be substantially extended as seen in FIGS. 5 and 6 so that the tip end 78 is distant from the first end portion 84 of the guide sleeve 68. At this point, an annular stop member on the vacuum conduit 74 engages the second end 86 and prevents further movement of the vacuum conduit.

The guide sleeve 68 together with the vacuum conduit 74 is also rotatable within the bearings 70 and 72 relative to the longitudinal axis. In this manner, viewing FIG. 5, the tip end of the guide sleeve 84 and the tip end of the vacuum conduit 74 can be moved through an arc 92 which may be, for example, 60 degrees from a vertical plane and extending in both lateral directions. This can be achieved by the operator gripping the body 86 of the guide sleeve 68 and merely twisting the near end and rotating it on its longitudinal axis.

In order to use the detection and removal system 38, the wing section 20 is first, preferably, tipped into a substantially vertical plane so that a trailing portion 94 is raised above a leading portion 96. By so doing, all of the loose FOD in the main wing box region 34 is caused to fall and land substantially adjacent the front spar 26. The wing section 20 is then returned to a substantially horizontal position as indicated in FIG. 1 such that substantially all of the FOD comes to rest within a first compartment 98 defined by the front spar 26, the lower skin 24, and a blade 28 within the main wing box region 34 closest to the front spar 26.

With the FOD thereby positioned proximate to the front spar 26, an operator takes hold of the components 40 and inserts them through an opening 32 and then through an access hole 36 in the front spar 26 until an image of the first compartment 98 can be viewed on the screen 54. The guide sleeve 68 is then manipulated by means of the knob 90 and the vacuum conduit 74 is extended until the tip end 78 of the vacuum conduit 74 is positioned to retrieve one or more items of debris. As explained above, the operator can extend the tip end 78 until it is closely adjacent to the debris. When close enough to the debris, the vacuum source 80 is then effective to create a suction at the tip end 78 to thereby withdraw the debris for disposal.

While a preferred embodiment of the invention has been disclosed in detail, it should be understood by those skilled in the art that various other modifications may be made to the illustrated embodiment without departing from the scope of the invention as described in the specification and defined in the appended claims.

I claim:

1. A system capable of insertion through a small-sized opening into an enclosed region for detecting and removing foreign object debris from the enclosed region comprising:

an elongated tubular borescope having an outer peripheral surface and extending between proximal and distal ends, said borescope including:

first and second windows in said outer peripheral surface adjacent said distal end;

a source of light remote from said distal end;

first optical transmission means within said borescope for transmitting light from said light source to and through said first window to illuminate a debris containing region to be inspected externally of said distal end of said borescope;

television means for presenting an image to a viewer;

second optical transmission means within said borescope for transmitting an image from the debris containing region to said television means;

a vacuum conduit extending between a near end and a tip end proximate to said distal end of said borescope and being flexible at least adjacent said tip end, said vacuum conduit being operably connected to a source of vacuum to create a suction at said tip end; and an elongated guide sleeve having a longitudinal axis for slidably receiving said vacuum conduit therethrough, said guide sleeve extending between first and second ends, said near end of said vacuum conduit being external of said guide sleeve and extending beyond said second end, said tip end of said vacuum conduit being movable relative to said guide sleeve between a retracted position whereat said tip end of said vacuum conduit is substantially coincident with said first end of said guide sleeve and an extended position whereat said tip end of said vacuum conduit is distant from said first end, said first end of said guide sleeve being capable of articulation from a neutral position aligned with said longitudinal axis and an operating position extending transverse of said longitudinal axis whereby said tip end of said vacuum conduit is similarly turned to an operating position extending transverse of said longitudinal axis;

said vacuum conduit being rotatable relative to said guide sleeve about said longitudinal axis to position said tip end thereof proximate to the debris at the debris containing region when said tip end is in the operating position to thereby withdraw the debris for disposal.

2. A system for detecting and removing foreign object debris as set forth in claim 1 including:
operating means for rotating said guide tube about said longitudinal axis.

3. A system for detecting and removing foreign object debris as set forth in claim 1 including:
articulating means for selectively turning said first end of said guide sleeve so as to extend transverse of said longitudinal axis.

4. A system for detecting and removing foreign object debris as set forth in claim 1 including:
a source of vacuum in communication with said near end of said vacuum conduit to create a suction at said tip end so as to withdraw the debris for disposal.

5. A system for detecting and removing foreign object debris as set forth in claim 1 wherein said first optical transmission means includes a fiber optic bundle.

6. A system capable of insertion through a small-sized opening into an enclosed region for detecting and removing foreign object debris from the enclosed region comprising:
an elongated tubular borescope extending between proximal and distal ends and including means for illuminating a debris containing region externally of said distal end of said borescope and means for transmitting for projection by television means an image of the debris containing region;

a vacuum conduit having a neutral longitudinal axis and including a tip end proximate to said distal end of said borescope and being flexible at least adjacent said tip end, said vacuum conduit being operably connected to a source of vacuum to create a suction at said tip end; and articulating means for moving said tip end between a neutral position aligned with said longitudinal axis and an operating position extending transverse of said longitudinal axis;

said vacuum conduit being rotatable about said longitudinal axis to position said tip end thereof proximate to the debris at the debris containing region when said tip end is in the operating position to thereby withdraw the debris for disposal.

7. A system for detecting and removing foreign object debris as set forth in claim 6 including:
operating means for rotating said vacuum conduit about said longitudinal axis.

8. A system for detecting and removing foreign object debris as set forth in claim 6 including:
articulating means for selectively turning said tip end of said vacuum conduit so as to extend transverse of said longitudinal axis.

9. A system for detecting and removing foreign object debris as set forth in claim 6 including:
a source of vacuum in communication with said vacuum conduit to create a suction at said tip end so as to withdraw the debris for disposal.

10. A system for detecting and removing foreign object debris as set forth in claim 6 wherein said illuminating means includes a source of light distant from said distal end and a fiber optic bundle optically connecting said light source and said distal end.

* * * * *